United States Patent [19]

Chiao

[11] Patent Number: 5,554,808
[45] Date of Patent: Sep. 10, 1996

[54] SYSTEM AND METHOD FOR DETECTING PLY WRINKLING IN A LAMINATED COMPOSITE

[75] Inventor: Richard Y. Chiao, Clifton Park, N.Y.

[73] Assignee: General Electric Company, Schenectady, N.Y.

[21] Appl. No.: 415,916

[22] Filed: Apr. 3, 1995

[51] Int. Cl.$^6$ .......................... G01N 29/04; G01N 29/06
[52] U.S. Cl. .................... 73/598; 73/620; 73/625
[58] Field of Search .................. 73/598, 588, 582, 73/602, 620, 629, 633, 618, 625

[56] References Cited

U.S. PATENT DOCUMENTS

| | | | |
|---|---|---|---|
| 4,457,174 | 7/1984 | Bar-Cohen et al. | 73/598 |
| 4,545,250 | 10/1985 | Miwa | 73/602 |
| 4,567,764 | 2/1986 | Jamison et al. | 73/582 |
| 4,723,553 | 2/1988 | Miwa et al. | 73/602 |
| 4,947,351 | 8/1990 | Moran et al. | 73/602 |

OTHER PUBLICATIONS

"Sensing Strategy to Detect Wrinkles in Components" by Pereira, et al, IEEE Transactions on Instrumentation and Measurement, vol. 43, No. 3, Jun. 1994.

Primary Examiner—Hezron E. Williams
Assistant Examiner—Nashimiya Ashraf
Attorney, Agent, or Firm—David C. Goldman; Marvin Snyder

[57] ABSTRACT

The present invention discloses a system and a method for ultrasonically detecting ply wrinkling in a laminated composite. The composite is ultrasonically scanned with sound wave energy generated from transducer(s) operating in an oblique incidence pulse echo mode. Echo signals reflected from the plies of the composite are then detected with the transducer(s). Each set of reflected echo signals represents a three-dimensional waveform data set u(x,y,t) having spatial dimensions (x,y) and a temporal dimension (t) mapping directly to a third spatial dimension (z) orthogonal to the surface of the composite. The three dimensional waveform data set u (x,y,t) corresponds to a three-dimensional volumetric region in the composite. The three-dimensional waveform data set u(x,y,t) is then processed into a rectified data set w(x,y,t). Ply noise in the three-dimensional data set w(x,y,t) is then filtered. The filtered three-dimensional data set is then converted into wrinkle severity C-scan and a wrinkle depth C-scan. Subsurface wrinkling in the composite is then detected and measured from the wrinkle severity C-scan and the wrinkle depth C-scan.

28 Claims, 4 Drawing Sheets

SYSTEM AND METHOD FOR DETECTING PLY WRINKLING IN A LAMINATED COMPOSITE

BACKGROUND OF THE INVENTION

The present invention relates generally to nondestructive evaluation of engineering materials, and more particularly to using ultrasonic techniques for detecting ply wrinkling in a laminated composite.

Typically, a laminated composite consists of several layers of plies laminated together. A common problem that often arises during the manufacture of a thick composite by compression molding is that plies may wrinkle. Ply wrinkling occurs when the compressive force on the composite exceeds the binder strength, resulting in a ply wrinkle. Ply wrinkling in a laminated composite is a major problem because of its potential to compromise mechanical properties of an intended design. In particular, a laminated composite with ply wrinkling is more susceptible to tensile and bending forces, making it impractical for the composite to perform its intended function, resulting in a lesser quality product.

Therefore, there is a need for a procedure that can accurately detect and measure wrinkles in a laminated composite. In particular, it is important to measure the severity and depth of wrinkles because wrinkles near the surface of the composite are much more susceptible to bending forces. One procedure for detecting wrinkles in components has been disclosed in Pereira et al., Sensing Strategy to Detect Wrinkles in Components, IEEE TRANSACTION ON INSTRUMENTATION AND MEASUREMENT, Vol. 43, No. 3, June 1994, pp. 442–448. Pereira et al. uses two displacement sensors (i.e., either laser or fiber optic) to detect the maximum amplitude of a wrinkle present in a component. The effectiveness of the procedure disclosed in Pereira et al. is limited to wrinkles that are visible on the surface and not wrinkles within the material. Thus, Pereira et al. is unable to fully characterize the severity and depth of any subsurface wrinkles in a composite, making it hard to ascertain the extent of how much a design has been compromised. In another procedure, wrinkle detection and measurement is attained by using an ultrasound transducer operating in a transmission or normal incidence pulse echo mode and imaging the ultrasound attenuation caused by the wrinkle. In this procedure, only the shadow of the wrinkle is detected and not the wrinkle. Consequently, the severity and depth of the wrinkle cannot be fully characterized.

SUMMARY OF THE INVENTION

Therefore, it is a primary objective of the present invention to provide a system and method for measuring the severity and depth of subsurface ply wrinkles in a laminated composite.

Another object of the present invention is to use an ultrasonic transducer operating in an oblique incidence pulse echo mode to detect subsurface ply wrinkles and characterize their severity and depth.

Thus, in accordance with a first embodiment of the present invention, there is provided a system and method for ultrasonically detecting and measuring subsurface ply wrinkling in a laminated composite. In the first embodiment, the composite is ultrasonically scanned with sound wave energy generated from a first transducer operating in a perpendicular incidence pulse echo mode to determine the direction of a ply wrinkle trough. After the direction of the ply wrinkle trough has been determined, the composite is ultrasonically scanned with sound wave energy generated from a second transducer operating in an oblique incidence pulse echo mode. Echo signals reflected from the plies of the composite are then detected with the second transducer. A set of reflected echo signals represents a three-dimensional waveform data set u(x,y,t) having spatial dimensions (x,y) and a temporal dimension (t) mapping directly to a third spatial dimension (z) orthogonal to the surface of the composite. The three dimensional waveform data set u(x,y,t) corresponds to a three-dimensional volumetric region in the composite. The three-dimensional waveform data set u(x,y,t) is then processed into a rectified data set w(x,y,t). Ply noise in the three-dimensional data set w(x,y,t) is then filtered. The filtered three-dimensional data set is then converted into two two-dimensional C-scans of the composite, wherein a first C-scan corresponds to wrinkle severity and a second C-scan corresponds to wrinkle depth. The extent of subsurface wrinkling in the composite is then measured from the wrinkle severity and the wrinkle depth C-scans.

In accordance with a second embodiment of the present invention, there is provided another system and method for ultrasonically detecting and measuring subsurface ply wrinkling in a laminated composite. In the second embodiment, the composite is ultrasonically scanned with sound wave energy generated from a first transducer operating in an oblique incidence pulse echo mode and a second transducer operating in an oblique incidence pulse echo mode. The first and second transducer are positioned in orthogonal planes perpendicular to the surface of the composite. Echo signals reflected from the plies of the composite are then detected with the first and second transducer. Each set of reflected echo signals from the first and second transducer represents a three-dimensional waveform data set u(x,y,t) having spatial dimensions (x,y) and a temporal dimension (t) mapping directly to a third spatial dimension (z) orthogonal to the surface of the composite. The three dimensional waveform data set u(x,y,t) corresponds to a three-dimensional volumetric region in the composite. The three-dimensional waveform data set u(x, y, t) is then processed into a rectified data set w(x,y,t). Ply noise in the three-dimensional data set w(x,y,t) is then filtered. The filtered three-dimensional data set is then converted into two two-dimensional C-scans of the composite, wherein a first C-scan corresponds to wrinkle severity and a second C-scan corresponds to wrinkle depth. The extent of subsurface wrinkling in the composite is then measured from the wrinkle severity and the wrinkle depth C-scans.

While the present invention will hereinafter be described in connection with a preferred embodiment and method of use, it will be understood that it is not intended to limit the invention to this embodiment. Instead, it is intended to cover all alternatives, modifications and equivalents as may be included within the spirit and scope of the present invention as defined by the appended claims.

DETAILED DESCRIPTION OF THE PRESENT INVENTION

Figure 1:
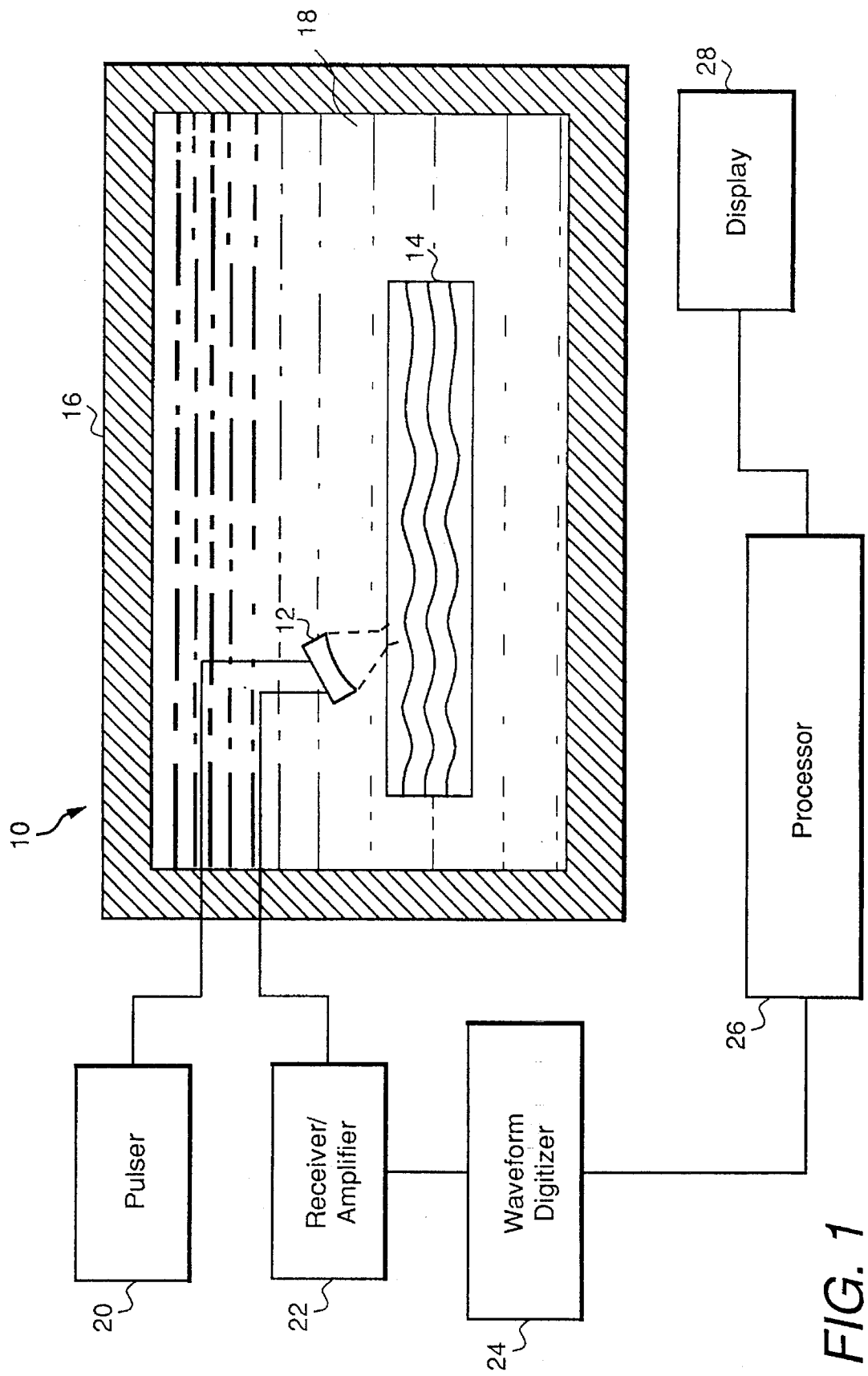
FIG. 1 is a block diagram of an ultrasonic detection system used in the present invention.

FIG. 1 shows a block diagram of an ultrasonic detection system 10 used in the present invention. In the ultrasonic inspection system 10, a transducer 12 is raster scanned over the surface of a laminated composite 14 which includes several layers of plies laminated together and which is immersed in a tank 16 full of a liquid 18 such as water. The transducer 12 transmits an ultrasonic beam generated from a pulser 20 towards the composite 14 at a plurality of scanning positions (x,y) along the surface of the composite. Ultrasonic sound waves reflected from the plies within the composite 14 are detected by the transducer 12 and amplified by a receiver/amplifier 22. The amplified sound waves are digitized by a digitizer 24 such as an A/D converter and stored in the memory of a processor 26. The digitized data are then processed by the processor 26. The processor, using a technique which is described below in further detail, isolates any subsurface wrinkles present in the composite 14. C-scans of the subsurface wrinkling are then generated and displayed on a display 28.

In the ultrasonic inspection system 10, the transducer 12 operates in an oblique incidence pulse echo mode and is oriented at an angle θ from a surface normal to the composite 14. The angle θ is preferably in the range of about 10 degrees to about 15 degrees, depending on the index of refraction from water to the composite 14. In addition, the transducer 12 is in a plane perpendicular to the direction of the wrinkle trough 30, which in the present invention is the y direction. Although this specification can be relaxed, the transducer 12 cannot be in a plane parallel to the wrinkle trough 30.

Figure 2A:
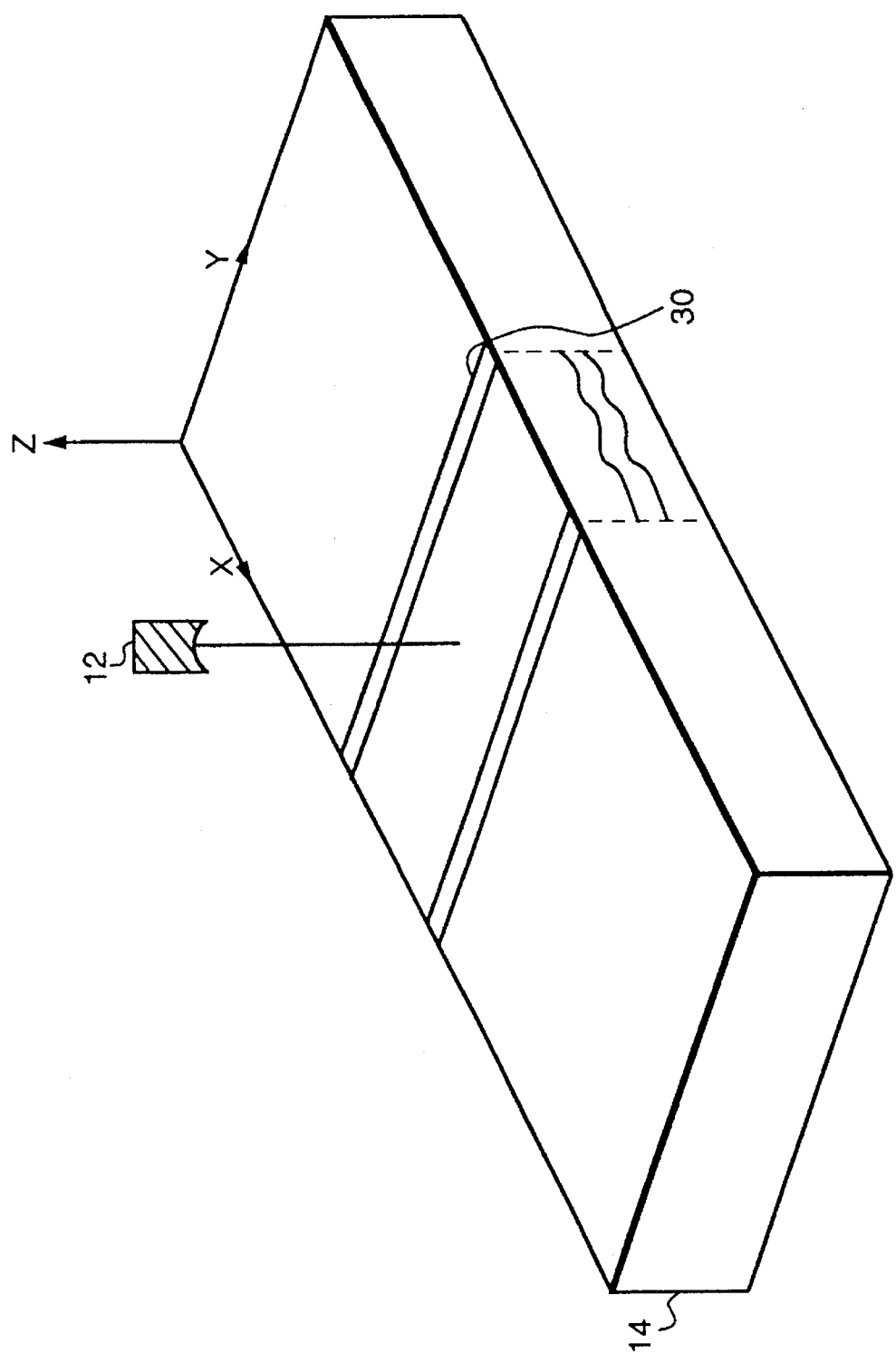
FIGS. 2a–2b is a diagram of an ultrasonic scanning configuration used in the present invention to detect ply wrinkling.
Figure 2B:
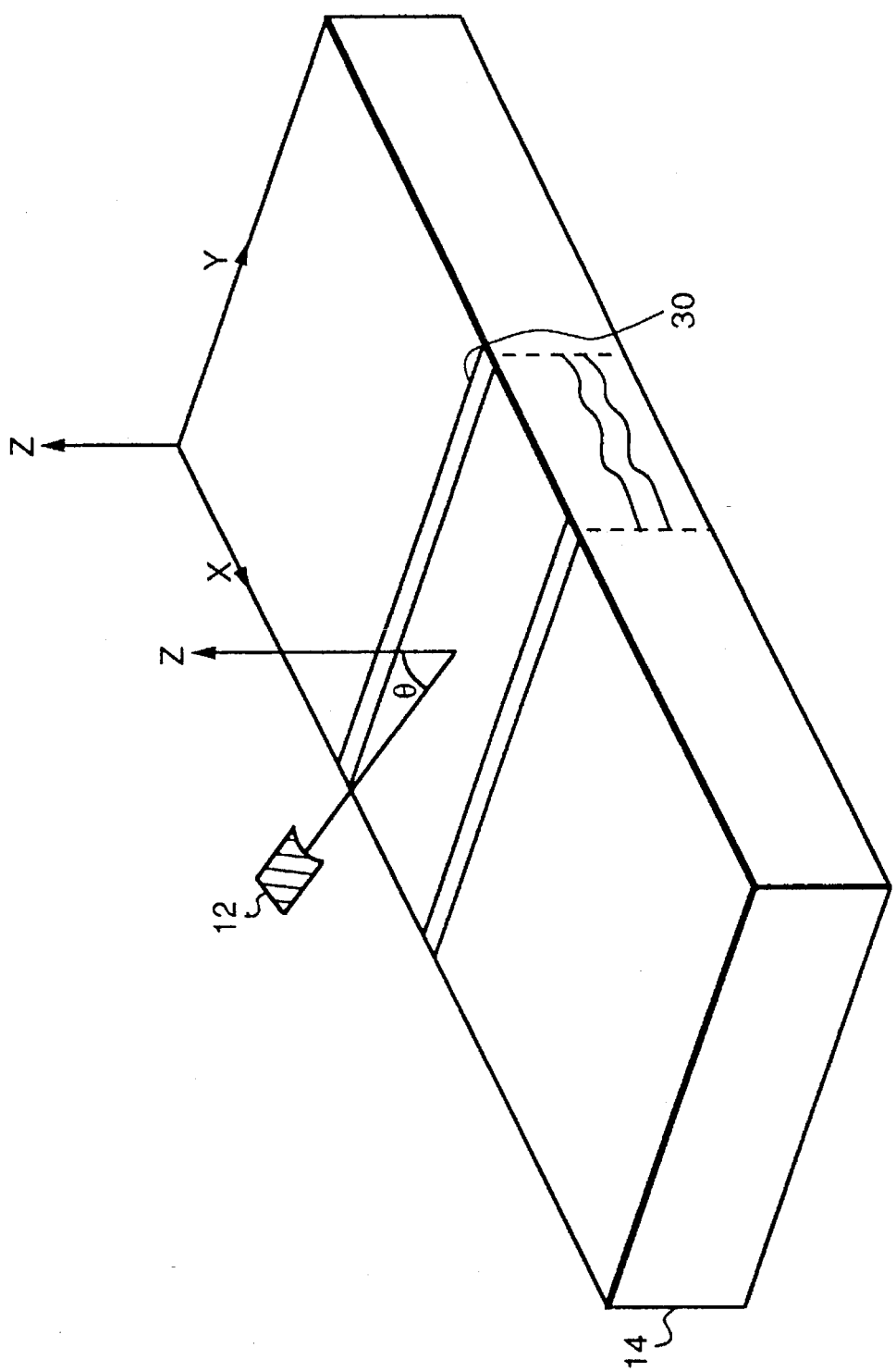
Figure 3:
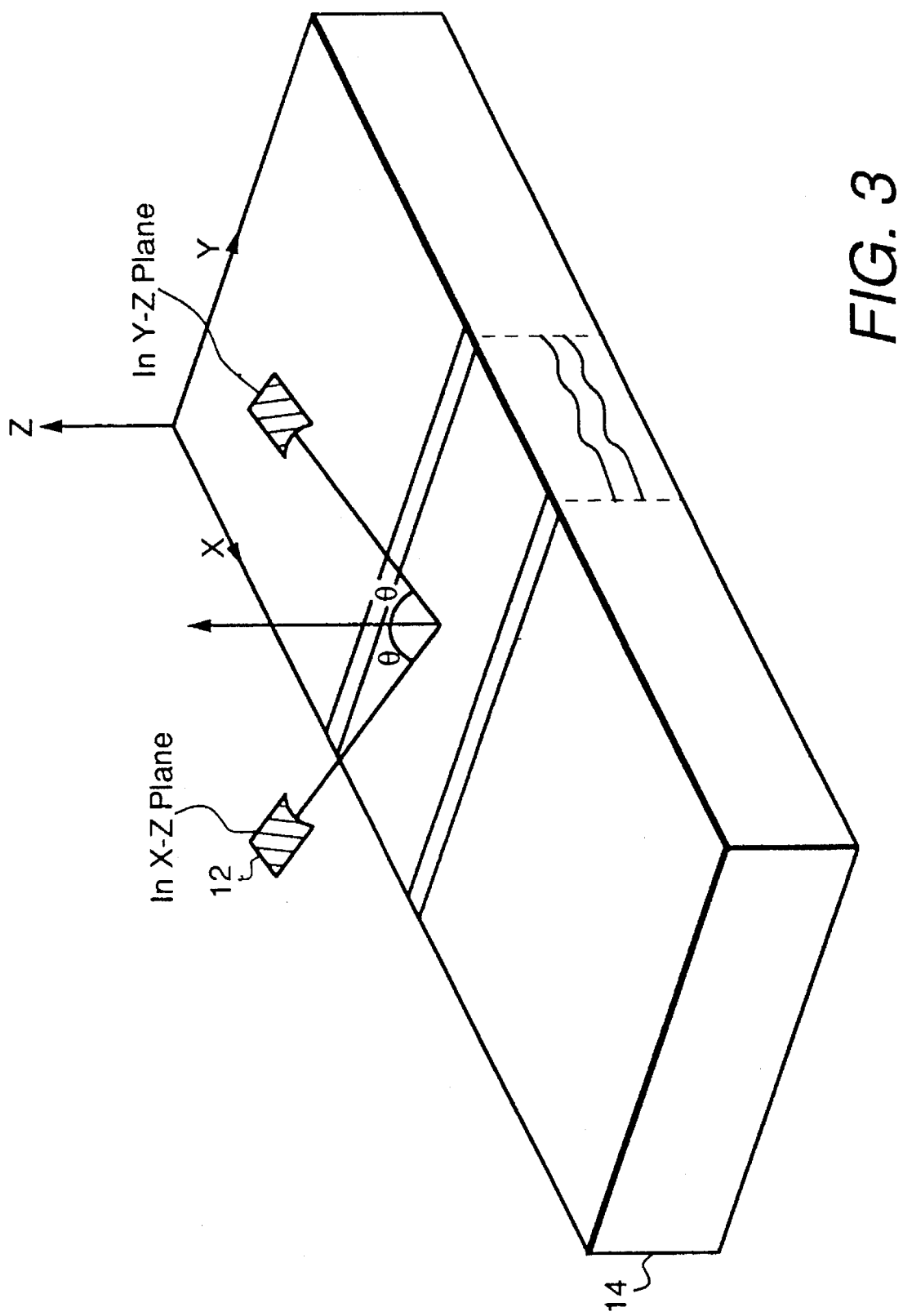
FIG. 3 is a diagram of another ultrasonic scanning configuration used in the present invention.

In the present invention, there are two possible scanning configurations in which the transducer 12 can detect wrinkling in the composite 14. One approach is to first scan the composite with the transducer 12 operating in a perpendicular incidence pulse echo mode to detect the wrinkle as shown in FIG. 2a. After the wrinkle has been detected and the direction of the wrinkle trough has been determined, then the composite 14 is re-scanned with the transducer 12 operating in the oblique incidence pulse echo mode as shown in FIG. 2b. A second approach is to use two transducers both operating with an oblique incidence pulse echo mode to simultaneously scan the composite 14, with each transducer oriented at an angle θ from a surface normal to the composite as shown in FIG. 3. Note that the two transducers lie in orthogonal planes perpendicular to the surface of the composites. In particular, one transducer is in the x–z plane and the second transducer is in the y–z plane.

In either scanning configuration, the transducers are raster scanned over the composite 14 in the x and y direction. At each x and y location of the raster scan, sound wave energy is generated from the transducers 12 and emitted into the composite 14. The center frequency of the transducers preferably operate in a range from about 1 MHz to about 5 MHz. The echo signals reflected back from the plies of the composite 14 are received by the transducers at that x and y location of the raster scan and amplified by the receiver/amplifier 22 and then digitized by the waveform digitizer 24. Each set of digitized echo signals represents a three-dimensional waveform data set u(x,y,t) having spatial dimensions (x,y) corresponding to the location along the surface of the composite 14 and a temporal dimension (t) that maps directly to a third spatial dimension (z) orthogonal to the surface of the composite. After the composite has been scanned, the result is a three-dimensional waveform data set u(x,y,t) which corresponds to a three-dimensional volumetric region in the composite 14.

The digitized three-dimensional waveform data set u(x,y,t) is then processed by the processor 26 to detect any subsurface wrinkles within the composite. The first operation performed by the processor 26 is to remove the constant background from the three-dimensional waveform data set u(x,y,t). The constant background is removed by eliminating the spatial mean at each time instant in accordance with the following equation:

$$v(x,y,t) = u(x,y,t) - [average\ in\ x\ and\ y]u(x,y,t), \quad (1)$$

wherein v(x,y,t) is the three dimensional data set with the spatial mean removed. In equation 1, the removed spatial mean v(x,y,t) is obtained by taking the original three-dimensional waveform data set u(x,y,t) and subtracting the average value of the x and y spatial location at each temporal value t. After removing the spatial mean, the processor 26 rectifies the signal v(x,y,t) and performs gain correction in accordance with the following equation:

$$w(x,y,t) = |v(x,y,t)| * exp(\alpha ct), \quad (2)$$

wherein w(x,y,t) is the rectified three dimensional data set and α is the attenuation coefficient of the composite and c is the propagation velocity.

After rectification, the processor 26 performs a filtering operation such as three dimensional median or morphological filtering to reduce ply reflection noise. The filtering operation is performed by using either a 3×3×3 or 5×5×5 median filter. A more detailed description of the 3×3×3 or 5×5×5 median filter is provided in U.S. patent application Ser. No. 08/126,629, now U.S. Pat. No. 5,471,878, which is incorporated herein by reference.

After the noise has been removed from the three-dimensional data set w(x,y,t), it is converted into two two-dimensional projected images of the composite 14 known as C-scans. In the present invention, one C-scan is a wrinkle severity image and the second C-scan is a wrinkle depth image. The wrinkle severity C-scan of the wrinkle is determined in accordance with the following equation:

$$s(x,y) = max\ w(x,y,t), \quad (3)$$

wherein s(x,y) is the two dimensional wrinkle severity C-scan image. In equation 3, the image is determined by taking the maximum value along t at every x and y location. The amplitude of the wrinkle signal within the C-scan indicates the severity of the wrinkle. So, the larger the amplitude relative to the background value, the more severe the wrinkle. The wrinkle depth C-scan is determined in accordance with the following equation:

$$D(x,y) = t @ w(x,y,t) = s(x,y), \quad (4)$$

wherein D(x,y) is the depth of the wrinkle. In equation 4, the depth of the wrinkle is determined by finding the time t at which s(x,y) occurs in w(x,y,t). Both the wrinkle severity and the wrinkle depth information are then used to help characterize the composite. In particular, the wrinkle severity and wrinkle depth measurements are used to determine if there are wrinkles near the surface of the composite. This is important because wrinkles near the surface of the composite are much more susceptible to bending forces. Thus, it is necessary to detect wrinkles near the surface of the composite so that the composite can perform its intended function.

It is therefore apparent that there has been provided in accordance with the present invention, a system and method for detecting and characterizing a wrinkle in a composite that fully satisfy the aims and advantages and objectives hereinbefore set forth. The invention has been described with reference to several embodiments, however, it will be appreciated that variations and modifications can be effected by a person of ordinary skill in the art without departing from the scope of the invention.

I claim:

1. A method of ultrasonically detecting and measuring subsurface ply wrinkling in a laminated composite, comprising the steps of:

ultrasonically scanning the laminated composite with sound wave energy generated from a first transducer operating in a perpendicular incidence pulse echo mode to determine a direction of a ply wrinkle trough;

ultrasonically scanning the composite with sound wave energy generated from a second transducer operating in an oblique incidence pulse echo mode after the direction of the ply wrinkle trough has been determined;

detecting echo signals reflected from the composite with the second transducer, a set of reflected echo signals representing a three-dimensional waveform data set $u(x,y,t)$ having spatial dimensions $(x,y)$ and a temporal dimension $(t)$ mapping directly to a third spatial dimension $(z)$ orthogonal to the surface of the composite, the three dimensional waveform data set $u(x,y,t)$ corresponding to a three-dimensional volumetric region in the composite;

processing the three-dimensional waveform data set $u(x,y,t)$ into a data set $w(x,y,t)$;

filtering ply noise from the three-dimensional data set $w(x,y,t)$;

converting the filtered three-dimensional data set into two two-dimensional C-scans of the composite, wherein a first C-scan corresponds to wrinkle severity and a second C-scan corresponds to wrinkle depth; and measuring subsurface wrinkling in the composite from the wrinkle severity C-scan and the wrinkle depth C-scan.

2. A method according to claim 1, wherein the second transducer is oriented at an angle $\theta$ from a surface normal to the composite, the angle $\theta$ having a range of about 10 degrees to about 15 degrees.

3. A method according to claim 2, wherein the second transducer is oriented in a plane perpendicular to a direction of the wrinkle trough within the composite.

4. A method according to claim 1, wherein the processing step includes removing constant background from the three-dimensional waveform data set $u(x,y,t)$, rectifying the three-dimensional waveform data set $u(x,y,t)$, and performing gain correction on the three-dimensional waveform data set $u(x,y,t)$.

5. A method according to claim 1, wherein the filtering step includes using a three dimensional median filtering operation.

6. A method of ultrasonically detecting and measuring subsurface ply wrinkling in a laminated composite, comprising the steps of:

ultrasonically scanning the laminated composite with sound wave energy generated from a first transducer operating in an oblique incidence pulse echo mode and a second transducer operating in an oblique incidence pulse echo mode, the first and second transducer positioned in orthogonal planes perpendicular to a surface of the composite;

detecting echo signals reflected from the composite with the first and second transducer, a set of reflected echo signals from the first and second transducer representing a three-dimensional waveform data set $u(x,y,t)$ having spatial dimensions $(x,y)$ and a temporal dimension $(t)$ mapping directly to a third spatial dimension $(z)$ orthogonal to the surface of the composite, the three dimensional waveform data set $u(x,y,t)$ corresponding to a three-dimensional volumetric region in the composite;

processing the three-dimensional waveform data set $u(x,y,t)$ into a data set $w(x,y,t)$;

filtering ply noise from the three-dimensional data set $w(x,y,t)$;

converting the filtered three-dimensional data set into two two-dimensional C-scans of the composite, wherein a first C-scan corresponds to wrinkle severity and a second C-scan corresponds to wrinkle depth; and measuring subsurface wrinkling in the composite from the wrinkle severity C-scan and the wrinkle depth C-scan.

7. A method according to claim 6, wherein the first and second transducer are oriented at an angle $\theta$ from a surface normal to the composite, the angle $\theta$ having a range of about 10 degrees to about 15 degrees.

8. A method according to claim 7, wherein the first and second transducer are oriented in a plane perpendicular to a direction of a wrinkle trough within the composite.

9. A method according to claim 6, wherein the processing step includes removing constant background from the three-dimensional waveform data set $u(x,y,t)$, rectifying the three-dimensional waveform data set $u(x,y,t)$, and performing gain correction on the three-dimensional waveform data set $u(x,y,t)$.

10. A method according to claim 6, wherein the filtering step includes using a three-dimensional median filtering operation.

11. A system for ultrasonically detecting and measuring subsurface ply wrinkling in a laminated composite, comprising:

a first ultrasonic transducer for scanning the composite with a perpendicular incidence pulse of sound wave energy to determine a direction of a ply wrinkle trough;

a second ultrasonic transducer for scanning the composite with an oblique incidence pulse of sound wave energy after the direction of the ply wrinkle trough has been determined;

means coupled to the second ultrasonic transducer for receiving echo signals reflected from the composite, a set of echo signals representing a three-dimensional waveform data set $u(x,y,t)$ having spatial dimensions $(x,y)$ and a temporal dimension $(t)$ mapping directly to a third spatial dimension $(z)$ orthogonal to the surface of the composite, the three dimensional waveform data set $u(x,y,t)$ corresponding to a three-dimensional volumetric region in the composite;

a processor coupled to the receiving means for processing the three-dimensional waveform data set $u(x,y,t)$ into a data set $w(x,y,t)$, the processor filtering ply noise from the three-dimensional data set $w(x,y,t)$, the processor converting the filtered three-dimensional data set into two two-dimensional C-scans of the composite, wherein a first C-scan corresponds to wrinkle severity and a second C-scan corresponds to wrinkle depth; and a display coupled to the processor for displaying the wrinkle severity C-scan and the wrinkle depth C-scan and for detecting and measuring subsurface wrinkling in the composite from the C-scans.

12. A system according to claim 11, wherein the second transducer is oriented at an angle $\theta$ from a surface normal to the composite, the angle $\theta$ having a range of about 10 degrees to about 15 degrees.

13. A system according to claim 12, wherein the second transducer is oriented in a plane perpendicular to a direction of the wrinkle trough in the composite.

14. A system according to claim 11, wherein the processor removes constant background from the three-dimensional waveform data set u(x,y,t), rectifies the three-dimensional waveform data set u(x,y,t), and performs gain correction on the three-dimensional waveform data set u(x,y,t).

15. A system according to claim 11, wherein the filtering includes using a three-dimensional median filtering operation.

16. A system for ultrasonically detecting and measuring subsurface ply wrinkling in a laminated composite, comprising:
    a first ultrasonic transducer for scanning the composite with an oblique incidence pulse of sound wave energy;
    a second ultrasonic transducer for scanning the composite with an oblique incidence pulse of sound wave energy, the first and second transducers positioned in orthogonal planes perpendicular to a surface of the composite;
    means coupled to the first and second ultrasonic transducers for receiving echo signals reflected from the composite, a set of echo signals from the first and second transducer representing a three-dimensional waveform data set u(x,y,t) having spatial dimensions (x,y) and a temporal dimension (t) mapping directly to a third spatial dimension (z) orthogonal to the surface of the composite, the three dimensional waveform data set u(x,y,t) corresponding to a three-dimensional volumetric region in the composite;
    a processor coupled to the receiving means for processing the three-dimensional waveform data set u(x,y,t) into a data set w(x,y,t), the processor filtering ply noise from the three-dimensional data set w(x,y,t), the processor converting the filtered three-dimensional data set into two two-dimensional C-scans of the composite, wherein a first C-scan corresponds to wrinkle severity and a second C-scan corresponds to wrinkle depth; and
    a display coupled to the processor for displaying the wrinkle severity C-scan and the wrinkle depth C-scan and for detecting and measuring subsurface wrinkling in the composite from the C-scans.

17. A system according to claim 16, wherein the first and second transducers are oriented at an angle θ from a surface normal to the composite, the angle θ having a range of about 10 degrees to about 15 degrees.

18. A system according to claim 17, wherein the first and second transducers are oriented in a plane perpendicular to a direction of a wrinkle trough in the composite.

19. A system according to claim 16, wherein the processor removes constant background from the three-dimensional waveform data set u(x,y,t), rectifies the three-dimensional waveform data set u(x,y,t), and performs gain correction on the three-dimensional waveform data set u (x,y,t).

20. A system according to claim 16, wherein the filtering includes using a three-dimensional median filtering operation.

21. A method according to claim 1, wherein the wrinkle severity is determined in accordance with:

$$s(x,y) = max\ w(x,y,t),$$

wherein s(x,y) is the two dimensional wrinkle severity C-scan image and the wrinkle severity determined by taking a maximum value along (t) at every (x,y) location.

22. A method according to claim 21, wherein the wrinkle depth is determined in accordance with:

$$D(x,y) = t@w(x,y,t),$$

wherein D(x,y) is the two dimensional depth of the wrinkle C-scan image and the wrinkle depth determined by finding the time t at which the wrinkle severity occurs in the data set w(x,y,t).

23. A method according to claim 6, wherein the wrinkle severity is determined in accordance with:

$$s(x,y) = max\ w(x,y,t),$$

wherein s(x,y) is the two dimensional wrinkle severity C-scan image and the wrinkle severity determined by taking a maximum value along (t) at every (x,y) location.

24. A method according to claim 23, wherein the wrinkle depth is determined in accordance with:

$$D(x,y) = t@w(x,y,t),$$

wherein D(x,y) is the two dimensional depth of the wrinkle C-scan image and the wrinkle depth determined by finding the time t at which the wrinkle severity occurs in the data set w(x,y,t).

25. A system according to claim 11, wherein the wrinkle severity is determined in accordance with:

$$s(x,y) = max\ w(x,y,t),$$

wherein s(x,y) is the two dimensional wrinkle severity C-scan image and the wrinkle severity determined by taking a maximum value along (t) at every (x,y) location.

26. A system according to claim 25, wherein the wrinkle depth is determined in accordance with:

$$D(x,y) = t@w(x,y,t),$$

wherein D(x,y) is the two dimensional depth of the wrinkle C-scan image and the wrinkle depth determined by finding the time t at which the wrinkle severity occurs in the data set w(x,y,t).

27. A system according to claim 16, wherein the wrinkle severity is determined in accordance with:

$$s(x,y) = max\ w(x,y,t),$$

wherein s(x,y) is the two dimensional wrinkle severity C-scan image and the wrinkle severity determined by taking a maximum value along (t) at every (x,y) location.

28. A system according to claim 27, wherein the wrinkle depth is determined in accordance with:

$$D(x,y) = t@w(x,y,t),$$

wherein D(x,y) is the two dimensional depth of the wrinkle C-scan image and the wrinkle depth determined by finding the time t at which the wrinkle severity occurs in the data set w(x,y,t).

* * * * *